United States Patent [19]

Hester, Jr.

[11] 4,250,094
[45] Feb. 10, 1981

[54] 1-(AMINOALKYL) SUBSTITUTED-6-PHENYL-4H-S-TRIAZOLO[4,3-A][1,4]BENZODIAZEPINES

[75] Inventor: Jackson B. Hester, Jr., Galesburg, Mich.

[73] Assignee: The Upjohn Company, Kalamazoo, Mich.

[21] Appl. No.: 55,110

[22] Filed: Jul. 5, 1979

Related U.S. Application Data

[63] Continuation of Ser. No. 309,213, Nov. 24, 1972, abandoned, which is a continuation-in-part of Ser. No. 138,288, Apr. 28, 1971, Pat. No. 4,141,902, and a continuation-in-part of Ser. No. 201,207, Nov. 12, 1971, abandoned, which is a continuation-in-part of Ser. No. 138,278, Apr. 28, 1971, abandoned.

[51] Int. Cl.$^3$ .................... C07D 487/04; A61K 31/55
[52] U.S. Cl. .................... 260/245.5; 260/239.3 D; 424/269
[58] Field of Search .................... 260/245.5

[56] References Cited

U.S. PATENT DOCUMENTS 3,681,343   8/1972   Hester .................... 260/239.3 T

FOREIGN PATENT DOCUMENTS 6916543   5/1970   Netherlands .................... 260/245.5

*Primary Examiner*—Alton D. Rollins
*Attorney, Agent, or Firm*—John T. Reynolds

[57] ABSTRACT

1-(Aminoalkyl) substituted-6-phenyl-4H-s-triazolo[4,3-a][1,4]benzodiazepines of the formula II:

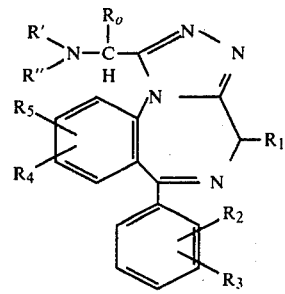

wherein $R_0$ is selected from the group consisting of hydrogen, methyl, or ethyl; wherein $R'$ and $R''$ are selected from the group consisting of hydrogen and alkyl of 1 to 3 carbon atoms, inclusive; wherein $R_1$ is selected from the group consisting of hydrogen, alkyl as defined above; wherein $R_2$, $R_3$, $R_4$, and $R_5$ are selected from the group consisting of hydrogen, alkyl as defined above, halogen, nitro, cyano, trifluoromethyl, and alkoxy, alkylthio, alkylsulfinyl, and alkylsulfonyl, in which the carbon chain moieties are of 1 to 3 carbon atoms, inclusive, are prepared by reacting a compound of the formula:

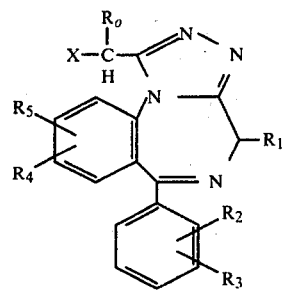

wherein X is chlorine or bromine and wherein $R_0$, $R_1$, $R_2$, $R_3$, $R_4$, and $R_5$ are defined as above with an amine of the formula:

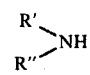

wherein $R'$ and $R''$ are defined as above.

The new products of formula II including their pharmacologically acceptable acid addition salts and N-oxides are useful as sedatives, tranquilizers, muscle relaxants and antidepressants in mammals and birds.

11 Claims, No Drawings

1-(AMINOALKYL) SUBSTITUTED-6-PHENYL-4H-S-TRIAZOLO[4,3-A][1,4]BENZODIAZEPINES

CROSS REFERENCE TO RELATED APPLICATIONS

This is a continuation of application Ser. No. 309,213, filed Nov. 24, 1972, abandoned which is a continuation-in-part of application Ser. No. 138,288, filed Apr. 28, 1971, now U.S. Pat. No. 4,141,902, granted Feb. 27, 1979, and of application Ser. No. 201,207, filed Nov. 12, 1971, now abandoned. Application Ser. No. 201,207 itself is a continuation-in-part of application Ser. No. 138,278, filed Apr. 28, 1971, now abandoned, the right of priority of which applications is hereby claimed.

BACKGROUND OF THE INVENTION

Field of the Invention

This invention is directed to new organic compounds and is particularly concerned with novel 1-(aminoalkyl)substituted-6-phenyl-4H-s-triazolo[4,3-a][1,4]benzodiazepines and a process for the production thereof.

The novel compounds and the process of production therefor can be illustratively represented as follows:

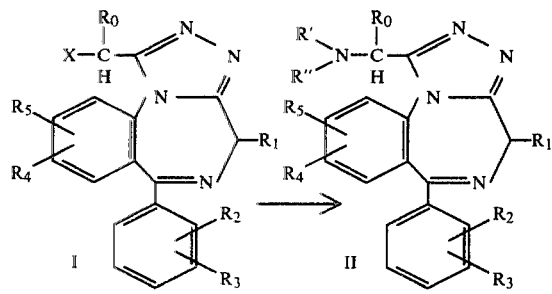

wherein X is chlorine or bromine; wherein $R_0$ is hydrogen, methyl or ethyl; wherein R' and R'' are selected from the group consisting of hydrogen and alkyl of 1 to 3 carbon atoms, inclusive, wherein $R_1$ is selected from the group consisting of hydrogen and alkyl defined as above; wherein $R_2$, $R_3$, $R_4$, and $R_5$ are selected from the group consisting of hydrogen, alkyl as defined above, halogen, nitro, cyano, trifluoromethyl, and alkoxy, alkylthio, alkylsulfinyl, and alkylsulfonyl, in which the carbon chain moieties are of 1 to 3 carbon atoms, inclusive.

The more preferred compounds of this invention have the formula III

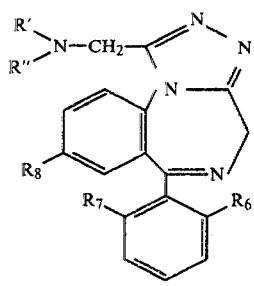

wherein R' and R'' are alkyl of 1 to 3 carbon atoms, inclusive; wherein $R_6$ and $R_7$ are selected from the group consisting of hydrogen, fluorine, chlorine, and bromine; and wherein $R_8$ is selected from the group consisting of hydrogen, fluorine, chlorine, bromine, —CN, —NO$_2$, —CF$_3$ and alkylthio in which the alkyl is defined as above.

The most desirable compounds can be represented by the formula IV:

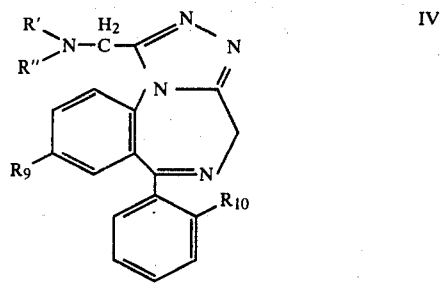

wherein R' and R'' are alkyl of 1 to 3 carbon atoms, inclusive and $R_9$ and $R_{10}$ are selected from the group consisting of hydrogen and chlorine.

The invention furthermore comprises the pharmacologically acceptable acid addition salts and N-oxides of compounds II, III, and IV.

The process of this invention comprises: treating a 1-chloro or 1-bromoalkyl compounds of formula I with the selected amine

wherein R' and R'' are hydrogen or alkyl of 1 to 3 carbon atoms.

DESCRIPTION OF THE PREFERRED EMBODIMENT

Lower alkyl groups of 1 to 3 carbon atoms, inclusive, are exemplified by methyl, ethyl, propyl, and isopropyl.

The carbon chain moiety of alkoxy, alkylthio, alkylsulfinyl, and alkylsulfonyl is alkyl of 1 to 3 carbon atoms, inclusive, as defined above.

The novel compounds of the formulae II, III, and IV including acid addition salts thereof have sedative, hypnotic, antianxiety, tranquilizing, anticonvulsant, and muscle relaxant effects in mammals and birds. Compounds of formulae III and IV have also strong antidepressant action in mammals.

The acid addition salts of compounds of formula II, III, and IV contemplated in this invention, are the hydrochlorides, hydrobromides, hydriodides, maleates, β-naphthalenesulfonates, sulfates, phosphates, cyclohexanesulfamates, methanesulfonates, toluenesulfonates and the like, prepared by reacting a compound of formula II, III, or IV with the stoichiometrically calculated amount of the selected pharmacologically acceptable acid. The N-oxides are prepared by reacting a compound of formula II, III, or IV with an excess of a peracid, for example peracetic or perbenzoic.

Sedative effects of e.g. 8-chloro-1-[(dimethylamino)-methyl]-6-phenyl-4H-s-triazolo[4,3-a][1,4]benzodiazepine are shown by the following tests in mice:

Chimney test: [Med. Exp. 4, 145 (1961)]: The effective intraperitoneal dosage for 50% of mice (ED$_{50}$) is 2.3 mg./kg. The test determines the ability of mice to back up and out of a vertical glass cylinder within 30 seconds. At the effective dosage, 50% of the mice failed doing it.

Dish test: Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of test compound at which 50% of the mice remain in the dish.

The $ED_{50}$ (intraperitoneal administration) in this test was 0.28 mg./kg.

Pedestal test: The untreated mouse leaves the pedestal in less than a minute to climb back to the floor of the standard mouse box. Tranquilized mice will stay on the pedestal for more than 1 minute. The $ED_{50}$ (intraperitoneal administration) is 0.8 mg./kg.

Nicotine antagonism test: Mice in a group of 6 are injected with the test compound [8-chloro-1-[(dimethylamino)methyl]-6-phenyl-4H-s-triazolo[4,3-a]-[1,4]benzodiazepine]. Thirty minutes later the mice including control (untreated) mice are injected with nicotine salicylate (2 mg./kg.). The control mice show overstimulation, i.e., (1) running convulsions followed by (2) tonic extensor fits; followed by (3) death. An intraperitoneal dosage of 0.11 mg./kg. of the test compound protected 50% of the animals against (3).

Antagonism to strychnine (as sulfate): The effective dosage $ED_{50}$ of 8-chloro-1-[(dimethylamino)methyl]-6-phenyl-4H-s-triazolo[4,3-a][1,4]benzodiazepine is 50 mg./kg. orally in mice. The test consists in orally administering into groups of 6 mice the test compound, and 30 minutes later 3 mg./kg. strychnine sulfate intraperitoneally. The survivors after 4 hours reflect the activity of the compound as a muscle relaxant and antispasmodic. A dosage of 3 mg./kg. of strychnine sulfate is routinely fatal to all the control mice.

The following compounds have (by intraperitoneal injection) $ED_{50}$ values as shown in the table I below.

TABLE I

| COMPOUND | $ED_{50}$ (in mg./kg.) | | | |
|---|---|---|---|---|
| | Ch | D | P | Ni |
| 8-chloro-1-[(dimethylamino)-methyl]-6-(o-chlorophenyl)-4H-s-triazolo[4,3-a][1,4]benzodiazepine | 0.2 | 0.36 | 0.36 | 0.63 |
| 1-[(dimethylamino)methyl]-6-(o-chlorophenyl)-4H-s-triazolo-[4,3-a][1,4]benzodiazepine | 0.35 | 0.8 | 22 | 0.15 |
| 8-chloro-1-[(diethylamino)-methyl]-6-(o-chlorophenyl)-4H-s-triazolo[4,3-a][1,4]benzodiazepine | 0.63 | 0.11 | 0.4 | 0.08 |

In particular the novel compounds of formulae III and IV and pharmacologically acceptable acid addition salts and N-oxides thereof have antidepressant activity and are thus useful for the treatment of depression in mammals or birds.

The main function of an anti-depressant is to return the depressed individual to normal functioning. This should be carefully differentiated from psychic stimulants such as the amphetamines which produce overstimulation in the normal individual.

Many different methods have been and are used to evaluate antidepressant activity. In general these methods involve antagonism to a depressant such as reserpine or tetrabenazine or a synergistic increase of the toxicity of certain compounds (i.e. yohimbine or 3,4-dihydroxyphenylalanine) and comparison of the drug action of the new compound with other known antidepressants. No single test alone can determine whether or not a new compound is an antidepressant or not, but the profile evidenced by various tests will establish the anti-depressant action if present. A number of such tests are described below.

Hypothermic tests with oxotermorine: [1-(4-pyrrolidino-2-butynyl)-2-pyrrolidinone].

Oxotremorine (as well as apomorphine and tetrabenazine) produces hypothermic responses in mice. This response is blocked by anticholinergics and anti-depressants such as atropine and imipramine respectively.

Oxotremorine produces a very pronounced hypothermia which reaches a peak 60 minutes after administration.

At a dose of 0.6 mg./kg. the body temperature of a mouse is decreased about 13° F. (when the mouse is kept at room temperature). This temperature decrease is antagonized by anti-depressants e.g. desipramine, imipramine, doxepine, and others, as can be seen from Table I.

TABLE II

| | Dose mg./kg., I. P. | Absorption Time (min) | Body Temperature °F.-Change From Vehicle Control After Minutes | | | |
|---|---|---|---|---|---|---|
| | | | 15 | 30 | 60 | 90 |
| oxotremorine-(control) | 0.6 | | −5.8 | −11.6 | −13.2 | −8.0 |
| Desipramine | 25 | 30 | −3.5 | −3.5 | −4.1 | −3.6 |
| Imipramine | 25 | 30 | −0.4 | −3.3 | −5.6 | −6.4 |
| Iprindole | 25 | 30 | −6.3 | −11.8 | −12.8 | −11.9 |
| Doxepine | 25 | 30 | −2.3 | −7.1 | −11.0 | −12.3 |
| Amitriptyline | 25 | 30 | +0.7 | −2.4 | −5.4 | −6.8 |
| Amphetamine | 5 | 30 | −1.5 | −4.3 | −4.4 | −2.2 |
| Atropine | 3 | 30 | +0.6 | −0.6 | −0.7 | −0.2 |

The present compounds were tested as follows. Four male mice of 18–22 g. (Strain CF=Carworth Farms) were injected intraperitoneally with 1 mg. of oxotremorine. The lowering of the body temperature was measured rectally with an electronic thermometer, before and 30 minutes after drug administration. After the drug administration the mice were kept at 19° C. in cages. A four degree difference between the control mice (oxotremorine alone) and the treated mice (oxotremorine and test compound) was used to indicate the antagonistic action of the test compound.

The test results are tabulated below:

The $ED_{50}$ is the dosage of the test compound at which half the mice had a temperature of at least 4° C. higher than the control mice.

TABLE III

| COMPOUNDS | $ED_{50}$ (mg./kg.) |
|---|---|
| 8-chloro-1-[(dimethylamino)methyl]-6-phenyl-4H-s-triazolo[4,3-a][1,4]benzodiazepine | 5.3 |
| 8-chloro-1-[(diethylamino)methyl]-6-phenyl-4H-s-triazolo[4,3-a][1,4]benzodiazepine | |
| Iprindole | |

TABLE III-continued

| COMPOUNDS | ED$_{50}$ (mg./kg.) |
| --- | --- |
| Irpindole | >50 |
| Imipramine | 5.3 |
| Doxepine | 14.9 |

Potentiation of yohimbine aggregation toxicity: the LD$_{50}$ of yohimbine hydrochloride in mice is 45 mg./kg. i.p. Administration of 30 mg./kg. of yohimbine hydrochloride was non-lethal. If an antidepressant is administered prior to the yohimbine hydrochloride (30 mg.) the lethality of the yohimbine hydrochloride is increased.

Ten male CF mice, 18–22 g., were injected with the anti-depressant and 30 minutes later with 30 mg. of yohimbine hydrochloride (YCl) in saline solution. After two hours, the LD$_{50}$ are determined. No mice or only one mouse is killed by 30 mg. of (YCl). If (YCl) is administered in the presence of an anti-depressant an increase of the toxicity of (YCl) is observed. The ED$_{50}$ values of the new compound and standard medicament which causes 50% of the mice to die is shown in TABLE IV.

TABLE IV

| | ED$_{50}$ (mg./kg.) |
| --- | --- |
| [YCl] (30 mg.) control | no death |
| [YCl] and 8-chloro-1-[(dimethylamino)-methyl]-6-phenyl-4H-s-triazolo[4,3-a]-[1,4]benzodiazepine | 12.5 |
| [YCl] and 8-chloro-1-[(diethylamino)-methyl]-6-phenyl-4H-s-triazolo[4,3-a]-[1,4]benzodiazepine | 42 |
| [YCl] and Iprindole | 20 |
| [YCl] and Imipramine | 4.4 |
| [YCl] Doxepine | 17.7 |

Potentiation of apomorphine gnawing: a group of 4 mice (male, CF, 18–22 g.) are administered the test compound intraperitoneally one hour prior to the subcutaneous injection of apomorphine hydrochloride 10 mg./kg. The mice are then placed in a plastic box (6"×11"×5") lined at the bottom with a cellophane-backed, absorbent paper. The degree of damage to the paper at the end of 30 min. is scored from zero to 4. The scores 3 and 4 indicate that the compound is a potentiator of apomorphine in this test (ED$_{50}$). The results are in Table V.

TABLE V

| COMPOUND | ED$_{50}$ (mg./kg.) |
| --- | --- |
| 8-chloro-1-[(dimethylamino)methyl] 6-phenyl-4H-s-triazolo[4,3-a][1,4]-benzodiazepine | 5.3 |
| 8-chloro-1-[diethylamino)methyl]-6-phenyl-4H-s-triazolo[4,3-a][1,4]benzodiazepine | 14.9 |
| Iprindole | >50 |
| Imipramine | 17.7 |
| Doxepine | 17.7 |

The LD$_{50}$ values in mice for these compounds are listed in table VI.

TABLE VI

| COMPOUND | LD$_{50}$ (mg./kg.) |
| --- | --- |
| 8-chloro-1-[dimethylamino)methyl]-6-phenyl-4H-s-triazolo[4,3-a][1,4]-benzodiazepine | 476 |
| 8-chloro-1-[(diethylamino)methyl]-6-phenyl-4H-s-triazolo[4,3-a][1,4]-benzodiazepine | >100 |

TABLE VI-continued

| COMPOUND | LD$_{50}$ (mg./kg.) |
| --- | --- |
| Iprindole | 450 |
| Imipramine | 178 |
| Doxepin | 126 |

The ED$_{50}$ and LD$_{50}$ of the new compounds compare thus favorably with standard antidepressant compounds on the market.

Other compounds of formula IV are anti-depressants as shown by table VII:

TABLE VII

| | YO | Oxo | Ap | LD$_{50}$ |
| --- | --- | --- | --- | --- |
| 8-chloro-1-(aminomethyl)-6-phenyl-4H-s-triazolo[4,3-a]-[1,4]benzodiazepine | 35.4 | 29.7 | 2.6 | >100 |
| 8-chloro-1-[(dimethylamino)-methyl]-6-(o-chlorophenyl)-4H-s-triazolo[4,3-a][1,4]benzodiazepine | >30 | >30 | 17.8 | >100 |
| 1-[(dimethylamino)methyl]-6-(o-chlorophenyl)-4H-s-triazolo-[4,3-a][1,4]benzodiazepine | >30 | >30 | >30 | >100 |

YO = Yohimbine test
Oxo = oxotremorine test
Ap = Apomorphine test

The pharmaceutical forms contemplated by this invention include pharmaceutical compositions suited for oral, parenteral, and rectal use, e.g., tablets, powder packets, cachets, dragees, capsules, solutions, suspension, sterile injectable forms, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Water or oils, e.g., coconut oil, sesame oil, safflower oil, cottonseed oil, peanut oil may be used for preparing solutions or suspensions of the active drug. Sweetening, coloring and flavoring agents may be added.

For mammals and birds, food premixes with starch, oatmeal, dried fishmeat, fishmeal, flour, and the like can be prepared.

As tranquilizers the compounds of formula II, III, and IV can be used in dosages of 0.02 mg. to 1 mg./kg. in oral or injectable preparations, as described above, to alleviate tension and anxiety in mammals, or birds, such as e.g., occurs when animals are in travel.

Other acid addition salts of the compounds of formulae II, III, and IV can be made such as the fluosilicic acid addition salts which are useful mothproofing compounds or the trichloroacetates useful as herbicides against Johnson grass, Bermuda grass, yellow foxtail, and green foxtail, and quack grass.

The starting materials of formula I of this invention are described in the beforementioned application Ser. No. 138,288, filed Apr. 28, 1971 now U.S. Pat. No. 4,141,902, and as further illustrated by the Preparations.

In carrying out the process of this invention a selected starting compound of formula I is treated with a selected alkyl or dialkylamine in which the alkyl group is of 1 to 3 carbon atoms, inclusive.

In the preferred embodiment of this invention, the reaction is carried out in solution, e.g. in tetrahydrofuran, dioxane, methanol, ethanol, 1- and 2-propanol, mixtures thereof and the like in the presence of an alkali iodide. The reaction is performed preferably at 0° to 30° C. over a period of 2 to 48 hours. Higher or lower temperatures are operative, but are not preferred. After the reaction is completed, the mixture is neutralized and the product II (III or IV) isolated and purified by conventional means, e.g. extraction, chromatography and crystallization.

The following Examples and Preparation are illustrative of the processes and products of the present invention, but are not to be construed as limiting.

PREPARATION 1:
7-Chloro-5-phenyl-3H-1,4-benzodiazepin-2-yl hydrazine

A stirred mixture of 7-chloro-1,3-dihydro-5-phenyl-2H-1,4-benzodiazepine-2-thione (50 g., 0.174 mole) and methanol (1700 ml.) was treated with hydrazine hydrate (34.9 g.) and allowed to remain at ambient temperature for 1 hour 45 minutes. A slow stream of nitrogen was bubbled through the mixture during this period. The resulting solution was concentrated in vacuo at 25°–30° C. The thus obtained residue was mixed with water and extracted with chloroform. The extract was dried over anhydrous potassium carbonate and concentrated under reduced pressure on the rotary evaporator in such a manner that the chloroform was replaced by ethyl acetate. The resulting mixture was crystallized at 4° C. to give 26.6 g. of 7-chloro-5-phenyl-3H-1,4-benzodiazepin-2-yl hydrazine of melting point 184°–186° C. and 3.04 g. of melting point 204°–211° C. The analytical sample was crystallized from ethyl acetate and had a melting point 217.5°–219° C.

Anal. calcd. for $C_{15}H_{13}ClN_4$: C, 63.27; H, 4.60; Cl, 12.45; N, 19.68.

Found: C, 63.30; H, 4.52; Cl, 12.46; N, 18.86.

Other starting thiones of this invention, substituted or unsubstituted 1,3,-dihydro-5-phenyl-2H-1,4-benzodiazepine-2-thiones, are described by G. A. Archer and L. H. Sternbach [J. Org. Chem. 29, 231 (1964) and U.S. Pat. No. 3,422,091]. These compounds are made by the reaction of the known substituted or unsubstituted 1,3-dihydro-5-phenyl-2H-1,4-benzodiazepin-2-ones by heating with phosphorus pentasulfide in pyridine for about 45 minutes (Archer et al., ibid.).

PREPARATION 2:
8-Chloro-1-(chloromethyl)-6-phenyl-4H-s-triazolo[4,3-a][1,4]benzodiazepine 7-Chloro-5-phenyl-3H-1,4-benzodiazepin-2-yl hydrazine [14.2 g., 0.05 mole] was added slowly to acetic acid (150 ml.) with external cooling. A solution of chloroacetyl chloride (5.65 g.) in acetic acid (7.5 ml.) was then added during 10 minutes, and the red solution was stirred at ambient temperature for 1.5 hours, treated with sodium acetate (4.1 g.), stirred again for 30 minutes and then refluxed for 3 hours and 15 minutes. This mixture was cooled, poured into ice water and concentrated to a small volume. It was then diluted with water, neutralized with sodium bicarbonate and extracted with chloroform. The extract was dried over anhydrous magnesium sulfate, concentrated and the residue chromatographed on silica gel (1 kg.) with 1% methanol-99% chloroform. The product obtained from the column was crystallized from ethyl acetate to give: 6.36 g. of 8-chloro-1-(chloromethyl)-6-phenyl-4H-s-triazolo[4,3-a][1,4]benzodiazepine. The analytical sample had a melting point 183°–186.5° C.

Anal. calcd. for $C_{17}H_{12}Cl_2N_4$: C, 59.49; H, 3.53; Cl, 20.66; N, 16.33.

Found: C, 59.59; H, 3.31; Cl, 20.21; N, 16.42.

PREPARATION 3:
8-Chloro-1-(bromomethyl)-6-phenyl-4H-s-triazolo[4,3-a][1,4]benzodiazepine In the manner given in Preparation 2, 7-chloro-5-phenyl-3H-1,4-benzodiazepin-2-yl hydrazine was reacted with bromoacetyl chloride and after 1.5 hours with sodium acetate, then refluxed to give 8-chloro-1-(bromomethyl)-6-phenyl-4H-s-triazolo[4,3-a][1,4]benzodiazepine.

PREPARATION 4:
8-Chloro-1-(α-chloroethyl)-6-phenyl-4H-s-triazolo[4,3-a][1,4]benzodiazepine 7-Chloro-5-phenyl-3H-1,4-benzodiazepin-2-yl hydrazine (2.85 g., 0.01 mole) was added, under nitrogen, with cooling and stirring to glacial acetic acid (30 ml.). A solution of 2-chloropropionyl chloride (1.27 g., 0.01 mole) in acetic acid (15 ml.) was then added dropwise, and the resulting red solution was stirred at room temperature for 1.5 hours, treated with sodium acetate (0.82 g., 0.01 mole), stirred for an additional 30 minutes and then refluxed for 2 hours. This mixture was cooled, poured into ice water and concentrated to a small volume. The residual solution was neutralized with sodium bicarbonate and extracted with methylene chloride. The extract was dried over anhydrous magnesium sulfate and concentrated. The residue was chromatographed on silica gel (400 g.) with 1% methanol-99% chloroform. The product thus obtained was crystallized from a small amount of ethyl acetate to give 1.39 g. of 8-chloro-1-[α-chloroethyl]-6-phenyl-4H-s-triazolo[4,3-a][1,4]benzodiazepine. The analytical sample had a melting point of 153.5°–156.5° C.

Anal. calcd. for $C_{18}H_{14}Cl_2N_4$: C, 60.52; H, 3.95; Cl, 19.85; N, 15.68.

Found: C, 60.34; H, 4.07; Cl, 19.81. N, 15.65.

PREPARATION 5:
8-Chloro-1-(chloromethyl)-6-phenyl-4H-s-triazolo[4,3-a][1,4]benzodiazepine 1. A stirred, ice-cold mixture of 7-chloro-5-phenyl-3H-1,4-benzodiazepin-2-yl hydrazine (28.5 g., 0.1 mole) in tetrahydrofuran (250 ml.) under nitrogen was treated, dropwise, during 17 min. with a solution of chloroacetyl chloride (11.3 g., 0.1 mole) in tetrahydrofuran (50 ml.). The resulting mixture was kept in the ice bath for 35 minutes and at ambient temperature for 1 hour. It was then poured into ice water, treated with a little chloroform and neutralized with sodium bicarbonate. The product crystallized, it was collected by filtration, washed with water and chloroform and dried in vacuo to give 23.7 g. of chloroacetic acid, 2-(7-chloro-5-phenyl-3H-1,4-benzodiazepin-2-yl)hydrazide. The chloroform layer of the filtrate was separated, washed with brine, dried over anhydrous sodium sulfate and concentrated in vacuo. The residue was crystallized from ethyl acetate to give 6.47 g. of additional product of melting point 202°–204° C. (dec.).

2. A stirred mixture of chloroacetic acid, 2-(7-chloro-5-phenyl-3H-1,4-benzodiazepin-2-yl) hydrazide (23.7 g.) in acetic acid (280 ml.), under nitrogen was placed in an oil bath that had been preheated to 140° C. After 20 minutes the mixture was cooled and concentrated in vacuo. The residue was mixed with water, neutralized with sodium bicarbonate and extracted with chloroform. The extract was washed with brine, dried over anhydrous sodium sulfate and concentrated. Crystallization of the residue from ethyl acetate gave 18.1 g. of 8-chloro-1-(chloromethyl)-6-phenyl-4H-s-triazolo[3,4-a][1,4]benzodiazepine of melting point 187°–189° C. (dec.) and 1.74 g. of melting point 187°–189° C. (dec.). This product was the same as that obtained in Preparation 2.

PREPARATION 6:

8-Chloro-1-(chloromethyl)-6-(o-chlorophenyl)-4H-s-triazolo[4,3-a][1,4]benzodiazepine In the manner given in Preparation 5, 7-chloro-5-(o-chlorophenyl)-3H-1,4-benzodiazepin-2-yl hydrazine (31.9 g., 0.1 mole) was reacted with chloroacetyl chloride (11.3 g. 0.1 mole) the resulting chloroacetic acid, 2-(7-chloro-5-(o-chlorophenyl)-3H-1,4-benzodiazepin-2-yl)hydrozide was cyclized in hot acetic acid to give 8-chloro-1-(chloromethyl)-6-(o-chlorophenyl)-4H-s-triazolo[4,3-a][1,4]benzodiazepine. The analytical sample had a melting point of 195°–198° C. with decomposition.

Anal. calcd. for $C_{17}H_{11}Cl_3N_4$: C, 54.06; H, 2.94; Cl, 28.17; N, 14.83.

Found: C, 53.95; H, 2.97; Cl, 28.38; N, 14.48.

PREPARATION 7:

8,10-Dimethyl-1-(bromomethyl)-6-[p-(methyl-thio)-phenyl]-4H-s-triazolo[4,3-a][1,4]benzodiazepine In the manner given in Preparation 2, 7,9-dimethyl-5-[p-(methylthio)phenyl]-3H-1,4-benzodiazepin-2-yl hydrazine was reacted with bromoacetyl bromide and after 1.5 hours with sodium acetate, than the mixture was refluxed to give 8,10-dimethyl-1-(bromomethyl)-6-[p-(methylthio)phenyl]-4H-s-triazolo[4,3-a][1,4]benzodiazepine.

PREPARATION 8:

8-Chloro-1-(chloromethyl)-6-(2,6-difluorophenyl)-4H-s-triazolo[4,3-a][1,4]benzodiazepine In the manner given in Preparation 2, 7-chloro-5-(2,6-difluorophenyl)-3H-1,4-benzodiazepin-2-yl hydrazine was reacted with chloroacetyl chloride and after 1.5 hours with sodium acetate; then, the mixture was refluxed to give 8-chloro-1-(chloromethyl)-6-(2,6-difluorophenyl)-4H-s-triazolo[4,3a][1,4]benzodiazepine.

PREPARATION 9:

8-Nitro-1-(bromomethyl)-6-(o-chlorophenyl)-4H-s-triazolo[4,3-a][1,4]benzodiazepine In the manner given in Preparation 2, 7-nitro-5-(o-chlorophenyl)-3H-1,4-benzodiazepin-2-yl hydrazine was reacted with bromoacetyl bromide and after 1.5 hours with sodium acetate, then refluxed to give 8-nitro-1-(bromomethyl)-6-(o-chlorophenyl)-4H-s-triazolo[4,3-a][1,4]benzodiazepine.

PREPARATION 10:

1-(chloromethyl)-6-(o-chlorophenyl)-4H-s-triazolo[4,3-a][1,4]benzodiazepine

1. A mixture of 5-(o-chlorophenyl)-1,3-dihydro-2H-1,4-benzodiazepine-2-thione (57.2 g.) in methanol (2180 ml.) was reacted with 40 g. of hydrazine hydrate to give 52.6 g. of 5-(o-chlorophenyl)-3H-1,4-benzodiazepin-2-yl hydrazine (A) of melting point 110.5° C.

2. 19.9 g. of this hydrazine (A) in tetrahydrofuran was reacted with chloroacetyl chloride in an ice bath to give 17.8 g. of chloroacetic acid, 2-[5-(o-chlorophenyl)-3H-1,4-benzodiazepin-2-yl]hydrazide [B].

3. This hydrazide (B, 17.8 g.) was heated with acetic acid (200 ml.) in an oil bath under nitrogen to 120° C. for 23 minutes to give 11.9 g. of 1-chloromethyl-6-(o-chlorophenyl)-4H-s-triazolo[4,3-a][1,4]benzodiazepine. The analytical sample had a melting point of 186°–188° C.

Anal. calcd. for $C_{17}H_{12}Cl_2N_4$: C, 59.49; H, 3.53; Cl, 20.66; N, 16.32.

Found: C, 59.00, 59.10; H, 3.47; 3.52; Cl, 21.34, 21.15; N, 16.20, 16.24.

PREPARATION 11:

8-Chloro-1-[α-chloropropyl]-6-(o-chlorophenyl)-4H-s-triazolo[4,3-a][1,4]benzodiazepine In the manner given in Preparation 2, 7-chloro-5-(o-chlorophenyl)-3H-1,4-benzodiazepin-2-yl-hydrazine was reacted with α-chlorobutyryl chloride (CHE—CH₂—CHCl—COCl) to give 8-chloro-1-(α-chloropropyl)-6-(o-chlorophenyl)-4H-s-triazolo[4,3-a][1,4]benzodiazepine.

PREPARATION 12:

1-Chloromethyl-6-phenyl-4H-s-triazolo[4,3-a][1,4]benzodiazepine

1. A stirred mixture of 5-phenyl-1,3-dihydro-2H-1,4-benzodiazepine-2-thione (7.45 g., 0.03 mole) in methanol (300 ml.) was allowed to react with hydrazine hydrate (6.0 g., 0.12 mole) to give 5-phenyl-3H-1,4-benzodiazepin-2-yl hydrazine as an oil. A solution of thio material in tetrahydrofuran (75 ml.) was cooled in an ice bath and treated with a solution of chloroacetyl chloride (3.39 g., 0.03 mole) in tetrahydrofuran (25 ml.) to give 6.43 g. of chloroacetic acid, 2-(5-phenyl-3H-1,4-benzodiazepin-2-yl) hydrazide (A).

2. A mixture of A (6.43 g., 0.0198 mole) and acetic acid (200 ml.) was stirred, under nitrogen at 120° for 20 minutes. The acetic acid was concentrated in vacuo and the residue was mixed with water, neutralized with sodium bicarbonate and extracted with chloroform. The extract was washed with water, dried and concentrated. Crystallization of the residue from methylene chlorideethyl acetate gave 2.16 g. of melting point 207°–210° C. and 0.85 g. of melting point 201°–204° C. of 1-chloromethyl-6-phenyl-4H-s-triazolo[4,3-a][1,4]benzodiazepine.

In the manner described in the foregoing preparations, other compounds of formula I can be prepared, such as:

8-chloro-1-(α-chloroethyl)-6-(o-chlorophenyl)-4H-s-triazolo[4,3-a][1,4]benzodiazepine;

8-fluoro-1-(bromomethyl)-6-(o-fluorophenyl)-4H-s-triazolo[4,3-a][1,4]benzodiazepine;

8-trifluoromethyl-1-[chloromethyl]-6-(o-bromophenyl)-4H-s-triazolo[4,3-a][1,4]benzodiazepine;

8-nitro-1-(chloromethyl)-6-[p-(trifluoromethyl)phenyl]-4H-s-triazolo[4,3-a][1,4]benzodiazepine;

7-methoxy-1-(chloromethyl)-6-[m-(methylthio)phenyl]-4H-s-triazolo[4,3-a][1,4]benzodiazepine;

9-(propylthio)-1-(α-chloropropyl)-6-(2,4-diethylphenyl)-4H-s-triazolo[4,3-a][1,4]benzodiazepine;

10-ethylthio-1-(α-chloropropyl)-6-(m-nitrophenyl)-4H-s-triazolo[4,3-a][1,4]benzodiazepine;

8-isopropylsulfinyl-1-(chloromethyl)-6-phenyl-4H-s-triazolo[4,3-a][1,4]benzodiazepine;

7,8-dicyano-1-(α-bromoethyl)-6-(p-bromophenyl)-4H-s-triazolo[4,3-a][1,4]benzodiazepine;

7-ethyl-10-methylsulfonyl-1-(α-bromopropyl)-6-[e-(ethylsulfonyl)-5-chlorophenyl]-4H-s-triazolo[4,3-a][1,4]benzodiazepine;

1-(α-chloroethyl)-6-(o-fluorophenyl)-4H-s-triazolo[4,3-a][1,4]benzodiazepine;

1-(α-bromopropyl)-6-(m-cyanophenyl)-4H-s-triazolo[4,3-a][1,4]benzodiazepine;

8-nitro-1-(chloromethyl)-6-phenyl-4H-s-triazolo[4,3-a][1,4]benzodiazepine;

8-fluoro-1-(chloromethyl)-6-phenyl-4H-s-triazolo[4,3-a][4,1]benzodiazepine;

8-bromo-1-(chloromethyl)-6-phenyl-4H-s-triazolo[4,3-a][1,4]benzodiazepine;

8-(trifluoromethyl)-1-(chloromethyl)-6-phenyl-4H-s-triazolo[4,3-a][1,4]benzodiazepine;

8-(methylthio)-1-(chloromethyl-6-phenyl-4H-s-triazolo[4,3-a][1,4]benzodiazepine;

8-chloro-1-(bromoethyl)-6-phenyl-4H-s-triazolo[4,3-a][1,4]benzodiazepine;

1-(chloromethyl)-6-(o-bromophenyl)-4H-s-triazolo[4,3-a][1,4]benzodiazepine;

1-(chloromethyl)-6-phenyl-4H-s-triazolo[4,3-a][1,4]benzodiazepine; and the like.

EXAMPLE 1:

8-Chloro-1-[(dimethylamino)methyl]-6-phenyl-4H-s-triazolo[4,3-a][1,4]benzodiazepine and 8-chloro-1-[(dimethylamino)methyl]-6-phenyl-4H-s-triazolo[4,3-a][1,4]benzodiazepine methanesulfonate An ice cold, stirred solution of 8-chloro-1-(chloromethyl)-6-phenyl-4H-s-triazolo[4,3-a][1,4]-benzodiazepine (1.37 g., 0.004 mole) in tetrahydrofuran (40 ml.) was treated with a solution of dimethylamine in methanol (32 ml.) and potassium iodide (0.66 g.) and kept at ambient temperatures (22°-24° C.) for 18 hours. The mixture was concentrated in vacuo and the residue was mixed with water, neutralized with a little sodium bicarbonate and extracted with chloroform. The extract was washed with brine, dried over anhydrous potassium carbonate and concentrated in vacuo. The residue was dissolved in ethylacetate, decolorized with activated charcoal (Darco G60) and crystallized to give 0.937 g. of 8-chloro-1-[(dimethylamino)methyl]-6-phenyl-4H-s-triazolo[4,3-a][1,4]benzodiazepine of melting point 171°-174° C. and 0.306 g. (88.3% yield), of melting point 171°-175° C. The analytical sample had melting point 171°-172.5° C.

Anal. calcd. for $C_{19}H_{18}ClN_5$: C, 64.86; H, 5.16; Cl, 10.08; N, 19.90.

Found: C, 64.91; H, 5.35; Cl, 10.03; N, 19.53.

A solution of 8-chloro-1-[(dimethylamino)methyl]-6-phenyl-4H-s-triazolo[4,3-a][1,4]benzodiazepine (351.8 mg., 0.001 mole) in methanol was heated with 1 ml. of a 1 N solution of methanesulfonic acid in methanol. The resulting salt was crystallized from methanol-ethyl acetate to give 0.439 g. of 8-chloro-1-[(dimethylamino)methyl]-6-phenyl-4H-s-triazolo[4,3-a][1,4]benzodiazepine methanesulfonate of melting point 196.5°-197.5° C. This material contained ethyl acetate of solution. Recrystallization of this salt from methanol-ethanol gave an analytical sample of melting point 242°-245° C.

Anal. calcd. for $C_{20}H_{22}ClN_5O_3S$: C, 53.63; H, 4.95; Cl, 7.91; N, 15.63; S, 7.16.

Found: C, 52.69; H, 5.07; Cl, 7.81; N, 15.66; S, 7.11.

EXAMPLE 2:

8-Chloro-1-[(dimethylamino)methyl]-6-(o-chlorophenyl)-4H-s-triazolo[4,3-a][1,4]benzodiazepine A stirred mixture of 1-(chloromethyl)-8-chloro-6-(o-chlorophenyl)-4H-s-triazolo[4,3-a][1,4]benzodiazepine (5.67 g., 0.015 mole) and dry tetrahydrofuran (150 ml.) was cooled in an ice bath and treated with methanolic dimethyl amine (15% v/v, 75 ml.) and potassium iodide (2.49 g.). The mixture was allowed to stand at room temperature under nitrogen for 18 hours. It was then concentrated and the residue was mixed with water and chloroform, neutralized with sodium bicarbonate and extracted with chloroform. The extract was washed with brine, dried over anhydrous sodium sulfate and concentrated in vacuo. The residue was crystallized from methanol-ethyl acetate to give in three crops:

1. 4.786 g. of melting point 202.5°-205° C.
2. 0.341 g. of melting point 201°-203° C.
3. 0.187 g. of melting point 202°-205° C. of 8-chloro-1-[(dimethylamino)methyl]-6-(o-chlorophenyl)-4H-s-triazolo[4,3-a][1,4]benzodiazepine.

After two recrystallizations from methanol-ethyl acetate the product had a melting point of 203.5°-205° C.

Anal. calcd. for $C_{19}H_{17}Cl_2N_5$: C, 59.08; H, 4.44; Cl, 18.36; N, 18.13.

Found: C, 59.12; H, 4.47; Cl, 18.59; N, 17.80.

EXAMPLE 3:

1-[(dimethylamino)methyl]-6-(o-chlorophenyl)-4H-s-triazolo[4,3-a][1,4]benzodiazepine A stirred mixture of 1-(chloromethyl)-6-(o-chlorophenyl)-4H-s-triazolo[4,3-a][1,4]benzodiazepine (5.14 g., 0.015 mole) in dry tetrahydrofuran (150 ml.) was cooled in an ice bath and treated with a 15% (v/v) solution of dimethylamine in methanol (75 ml.) and potassium iodide (2.49 g.). The mixture was stirred under nitrogen at ambient temperature for 18 hours and concentrated in vacuo. The residue was mixed with water and chloroform, neutralized with sodium bicarbonate, and extracted with chloroform. The extract was washed with brine, dried over anhydrous sodium sulfate and concentrated in vacuo. The residue was crystallized from ethyl acetate-Skellysolve B hexanes to give 4.43 g. of 1-[(dimethylamino)methyl]-6-(o-chlorophenyl)-4H-s-triazolo[4,3-a][1,4]benzodiazepine of melting point 143°-145° C.

A sample of this material which was recrystallized from ethyl acetate-Skellysolve B hexanes for analysis had melting point 143°-146° C.

Anal. calcd. for $C_{19}H_{18}ClN_5$: C, 64.86; H, 5.16; Cl, 10.08; N, 19.90.

Found: C, 64.70; H, 5.09; Cl, 10.11; N, 20.00.

EXAMPLE 4:

8-Chloro-1-[(diethylamino)methyl]-6-phenyl-4H-s-triazolo[4,3-a][1,4]benzodiazepine 8-Chloro-1-(chloromethyl)-6-phenyl-4H-s-triazolo[4,3-a][1,4]benzodiazepine (343 mg., 0.001 mole) was added to a solution of diethylamine (1 ml.) in dry dimethylformamide (5 ml.) and the mixture was stirred at ambient temperature under nitrogen, for 4 hours 30 minutes. Sodium iodide (50 mg.) was added and the mixture was stirred at ambient temperature for 17 hours 30 minutes and heated to 100°-111° C. for 6 hours. It was then poured into ice water and extracted with chloroform. The extract was washed with water, dried over anhydrous potassium carbonate and concentrated in vacuo. The residue was crystallized from ethyl acetate-Skellysolve B hexanes to give 0.277 g. of 8-chloro-1-[(diethylamino)methyl]-6-phenyl-4H-s-triazolo[4,3-a][1,4]benzodiazepine of melting point 128.5°–131.5° C. The analytical sample had a melting point of 131.5°–132.5° C.

Anal. calcd. for $C_{21}H_{22}ClN_5$: C, 66.39; H, 5.84; Cl, 9.33; N, 18.44.

Found: C, 66.20; H, 6.06; Cl, 9.29; N, 18.55.

In the manner given in Example 4, 8-chloro-1-[(dipropylamino)methyl]-6-phenyl-4H-s-triazolo[4,3-a][1,4]-benzodiazepine is prepared by reacting dipropylamine with 8-chloro-1-(chloromethyl)-6-phenyl-4H-s-triazolo[4,3-a]-[1,4]-benzodiazepine.

EXAMPLE 5:
8-Chloro-1-[(diethylamino)methyl]-6-phenyl-4H-s-triazolo[4,3-a][1,4]benzodiazepine A solution of 1,3-dihydro-7-chloro-5-phenyl-2H-1,4-benzodiazepine-2-thione and (diethylamino)acetic acid hydrazide in n-butyl alcohol was refluxed to give 8-chloro-1-[(diethylamino)methyl]-6-phenyl-4H-s-triazolo[4,3-a]-[1,4]benzodiazepine, which was recrystallized from ethyl acetate-Skellysolve B hexanes and was identical to the compound obtained in Example 4.

EXAMPLE 6:
6-Nitro-1-[(dimethylamino)methyl]-6-(o-chlorophenyl)-4H-s-triazolo[4,3-a][1,4]benzodiazepine In the manner given in Example 5, a solution of 1,3-dihydro-7-nitro-5-(o-chlorophenyl)-2H-1,4-benzodiazepine-2-thione in n-butyl alcohol was heated to reflux with (dimethylamino)acetic acid hydrazide to give 8-nitro-1-[(dimethylamino)methyl]-6-(o-chlorophenyl)-4H-s-triazolo-[4,3-a][1,4-benzodiazepine.

EXAMPLE 7:
9-Methyl-1-[(dipropylamino)methyl]-6-(p-isopropylphenyl)-4-H-s-triazolo[4,3-a][1,4-benzodiazepine In the manner given in Example 5, a solution of 1,3-dihydro-8-methyl-5-(p-isopropylphenyl)-2H-1,4-benzodiazepine-2-thione in n-butyl alcohol was heated to a reflux with (dipropylamino)acetic acid hydrazide to give 9-methyl-1-[(dipropylamino)methyl]-6-(p-isopropylphenyl)-4H-s-triazolo[4,3-a][1,4)benzodiazepine.

EXAMPLE 8:
1-[(dimethylamino)methyl]-8,10-dimethyl-6-[p-(methylthio)phenyl]-4H-s-triazolo[4,3-a][1,4]-benzodiazepine In the manner given in Example 1, 8,10-dimethyl-1-(bromomethyl)-6-[p-(methylthio)phenyl]-4H-s-triazolo[4,3-a]-[1,4]benzodiazepine was reacted with dimethylamine in the presence of sodium iodide to give 1-[(dimethylamino)methyl]-8,10-dimethyl-6-[p-(methylthio)phenyl]-4H-s-triazolo[4,3-a][1,4]benzodiazepine.

EXAMPLE 9:
8-Chloro-1-[(dimethylamino)methyl]-6-(2,6-difluorophenyl)-4H-s-triazolo[4,3-a][1,4-benzodiazepine In the manner given in Example 1, 8-chloro-1-(chloromethyl)-6-(2,6-difluorophenyl)-4H-s-triazolo-[4,3-a][1,4]benzodiazepine was reacted with dimethylamine in the presence of potassium iodide to give 8-chloro-1-[(dimethylamino)methyl]-6-(2,6-difluorophenyl)-4H-s-tri-azolo[4,3-a][1,4]benzodiazepine.

EXAMPLE 10:
1-[(dimethylamino)methyl]-8-nitro-6-phenyl-4H-s-triazolo[4,3-a][1,4]benzodiazepine In the manner given in Example 1, 8-nitro-1-(bromomethyl)-6-(o-chlorophenyl)-4H-s-triazolo[4,3-a][1,4]benzodiazepine was reacted with dimethylamine in the presence of sodium iodide to give 1-[(dimethylamino)methyl]-8-nitro-6-(o-chlorophenyl)-4H-s-triazolo[4,3-a][1,4]benzodiazepine.

EXAMPLE 11:
1-[(diethylamino)methyl]-6-(o-chlorophenyl)-4H-s-triazolo[4,3-a][1,4)benzodiazepine In the manner given in Example 1, 1-(chloromethyl)-6-(o-chlorophenyl)-4H-s-triazolo[4,3-a][1,4]-benzodiazepine was reacted with diethylamine in the presence of sodium iodide to give 1-[(diethylamino)methyl]-6-(o-chlorophenyl)4H-s-triazolo[4,3-a][1,4]benzodiazepine.

EXAMPLE 12:
8-Chloro-1-[α-(dipropylamino)propyl]-6-(o-chlorophenyl)-4H-s-triazolo[4,3-a][1,4]benzodiazepine In a manner given in Example 1, 8-chloro-1-(α-chloropropyl)-6-(o-chlorophenyl)-4H-s-triazolo[4,3-a][1,4]-benzodiazepine was reacted with dipropylamine in the presence of sodium iodide to give 8-chloro-1-[α-(dipropylamino)propyl]-6-(o-chlorophenyl)-4H-s-triazolo[4,3-a][1,4]benzodiazepine.

EXAMPLE 13:
8-Chloro-1-[α-(dimethylamino)ethyl]-6-(o-chlorophenyl)-4H-s-triazolo[4,3-a][1,4]benzodiazepine In the manner given in Example 1, 8-chloro-1-(α-chloroethyl)-6-(o-chlorophenyl)-4H-s-triazolo[4,3-a][1,4]-benzodiazepine was reacted with dimethylene in the presence of sodium iodide to give 8-chloro-1-[α-(dimethylamino)ethyl]-6-(o-chlorophenyl)-4H-s-triazolo[4,3-a][1,4]benzodiazepine.

EXAMPLE 14:
1-[(diethylamino)methyl]-8-fluoro-6-(o-fluorophenyl)-4H-s-triazolo[4,3-a][1,4]benzodiazepine In the manner given in Example 1, 8-fluoro-1-(bromomethyl)-6-(o-fluorophenyl)-4H-s-triazolo[4,3-a][1,4]benzodiazepine was reacted with diethylamine in the presence of sodium iodide to give 1-[(diethylamino)methyl]-8-fluoro-6-(o-fluorophenyl)-4H-s-triazolo-[4,3-a][1,4]benzodiazepine.

EXAMPLE 15:
1-[(dipropylamino)methyl]-8-trifluoromethyl-6-(o-bromophenyl)-4H-s-triazolo[4,3-a][1,4]benzodiazepine In the manner given in Example 1, 8-trifluoromethyl-1-(chloromethyl)-6-(o-bromophenyl)-4H-s-triazolo[4,3-a]-[1,4]benzodiazepine was reacted with dipropylamine in the presence of sodium iodide to give 1-[(dipropylamino)methyl]-8-trifluoromethyl-6-(o-bromophenyl)-4H-s-triazolo-[4,3-a][1,4]benzodiazepine.

EXAMPLE 16:
1-[(dimethylamino)methyl]-7-methoxy-6-[m-(methylthio)phenyl]-4H-s-triazolo[4,3-a][1,4]benzodiazepine In the manner given in Example 1, 7-methoxy-1-(chloromethyl)-6-[m-(methylthio)phenyl]-4H-s-triazolo-[4,3-a][1,4]benzodiazepine was reacted with dimethylamine in the presence of sodium iodide to give 1-[(dimethylamino)methyl]-7-methoxy-6-[m-(methylthio)phenyl]-4H-s-triazolo[4,3-a][1,4]benzodiazepine.

EXAMPLE 17:
1-[α-(dimethylamino)propyl]-9-(propylthio)-6-(2,4-diethylphenyl)-4H-s-triazolo[4,3-a][1,4]benzodiazepine In the manner given in Example 1, 9-(propylthio)-1-(α-chloropropyl)-6-(2,4-diethylphenyl)-4H-s-triazolo[4,3-a]-[1,4]-benzodiazepine was reacted with dimethylamine in the presence of sodium iodide to give 1-[α-(dimethylamino)propyl]-9-(propylthio)-6-(2,4-diethylphenyl)-4H-s-triazolo-[4,3-a][1,4]benzodiazepine.

EXAMPLE 18:
1-[(Dimethylamino)methyl]-8-isopropylsulfinyl-6-phenyl-4H-s-triazolo[4,3-a][1,4]benzodiazepine In the manner given in Example 1, 8-isoproplsulfinyl-1-(chloromethyl)-6-phenyl-4H-s-triazolo[4,3-a][1,4]-benzodiazepine was reacted with dimethylamine in the presence of sodium iodide to give 1-[(dimethylamino)methyl]-8-isopropylsulfinyl-6-phenyl-4H-s-triazolo[4,3-a][1,4]benzodiazepine.

EXAMPLE 19:
7,8-dicyano-1-[α-(diethylamino)ethyl]-6-(p-bromophenyl)-4H-s-triazolo[4,3-a][1,4-benzodiazepine In the manner given in Example 1, 7,8-dicyano-1-(α-bromoethyl)-6-(p-bromophenyl)-4H-s-triazolo[4,3-a][1,4]-benzodiazepine was reacted with diethylamine in the presence of sodium iodide to give 7,8-dicyano-1-[α-(diethylamino)ethyl]-6-(p-bromophenyl)-4H-s-triazolo[4,3-a][1,4]-benzodiazepine.

EXAMPLE 20:
7-ethyl-1-[α-(dimethylamino)propyl]-10-(methylsulfonyl)-6-(3-ethylsulfonyl-5-chlorophenyl)-4H-s-triazolo[4,3-a][1,4]benzodiazepine In the manner given in Example 1, 7-ethyl-10-methylsulfonyl-1-(α-bromopropyl)-6-(3-ethylsulfonyl-5-chlorophenyl)-4H-s-triazolo[4,3-a][1,4]-benzodiazepine was reacted with dimethylamine in the presence of sodium iodide to give 7-ethyl-1-[α-(dimethylamino)propyl]-10-methylsulfonyl-6-(3-ethylsulfonyl-5-chlorophenyl)-4H-s-triazolo-[4,3-a][1,4]benzodiazepine.

EXAMPLE 21:
8-Chloro-1-[(methylamino)methyl]-6-phenyl-4H-s-triazolo[4,3-a][1,4]benzodiazepine In the manner given in Example 1, 8-chloro-1-(chloromethyl)-6-phenyl-4H-s-triazolo[4,3-a][1,4]benzodiazepine was reacted with methylamine in the presence of sodium iodide to give 8-chloro-1-[(methylamino)methyl]-6-phenyl-4H-s-triazolo[4,3-a][1,4]benzodiazepin of melting point 152°–156° C.

EXAMPLE 22:
1-[(Dimethylamino)methyl]-6-phenyl-4H-s-triazolo[4,3-a][1,4]benzodiazepine In the manner given in Example 1, 1-(chloromethyl)-6-phenyl-4H-s-triazolo[4,3-a][1,4]benzodiazepine was reacted with dimethylamine to give 1-[(dimethylamino)-methyl]-6-phenyl-4H-s-triazolo[4,3-a][1,4]benzodiazepine of melting point 182°–183.5° C.

Anal. calcd. for $C_{19}H_{19}N_5$: C, 71.90; H, 6.03; N, 22.07.

Found: C, 72.16; H, 6.31; N, 22.90.

EXAMPLE 23:
1-(Aminomethyl)-8-chloro-6-phenyl-4H-s-triazolo[4,3-a][1,4]benzodiazepine In the manner given in Example 1, 1-(chloromethyl)-6-phenyl-4H-s-triazolo[4,3-a][1,4]benzodiazepine was reacted with ammonia in the presence of potassium iodide to give 1-(aminomethyl)-8-chloro-6-phenyl-4H-s-triazolo-[4,3-a][1,4]benzodiazepine of melting point 167.5°–172.5° C.

Anal. calcd. for $C_{17}H_{14}ClN_5$: C, 63.06; H, 4.36; Cl, 10.95; N, 21.63.

Found: C, 62.84; H, 4.56; Cl, 11.02; N, 21.10.

In the same manner given in the prior Examples other compounds corresponding to formulae II, III, or IV can be prepared. Representative compounds thus prepared include.

8-nitro-1-[(dimethylamino)methyl]-6-[(p-trifluoromethyl)-phenyl]-4H-s-triazolo[4,3-a][1,4]benzodiazepine;

10-ethylthio-1-[α-(diethylamino)ethyl]-6-(m-nitrophenyl)-4H-s-triazolo[4,3-a][1,4]benzodiazepine;

7,8-dicyano-1-[α-(dimethylamino)ethyl]-6-(p-bromophenyl)-4H-s-triazolo[4,3-a][1,4]benzodiazepine;

1-[α-(dipropylamino)ethyl]-6-(o-fluorophenyl)-4H-s-triazolo[4,3-a][1,4]benzodiazepine;

7-ethyl-10-(methylsulfonyl)-1-[α-(diethylamino)propyl-6-[3-(ethylsulfonyl)-5-chlorophenyl]-4H-s-triazolo-[4,3-a]-[1,4]benzodiazepine;

8-chloro-1-[α-(methylamino)ethyl]-6-(o-chlorophenyl)-4H-s-triazolo[4,3-a][1,4]benzodiazepine;

8-chloro-1-[α-(ethylamino)ethyl]-6-(o-chlorophenyl)-4H-s-triazolo[4,3-a][1,4]benzodiazepine;

8-chloro-1-[α-(propylamino)ethyl]-6-(o-chlorophenyl)-4H-s-triazolo[4,3-a][1,4]benzodiazepine;

8-nitro-1-[(methylamino)methyl]-6-[p-(trifluoromethyl)-phenyl]-4H-s-triazolo[4,3-a][1,4]benzodiazepine;

8-nitro-1-[(ethylamino)methyl]-6-[p-(trifluoromethyl)-phenyl]-4H-s-triazolo[4,3-a][1,4]benzodiazepine;

8-nitro-1-[(propylamino)methyl]-6-[p-(trifluoromethyl)-phenyl]-4H-s-triazolo[4,3-a][1,4]benzodiazepine;

9-(propylthio)-1-[α-(methylamino)propyl]-6-(2,4-diethylphenyl)-4H-s-triazolo[4,3-e][1,4]benzodiazepine;

7,8-dicyano-1-[α-(methylamino)ethyl]-6-(p-bromophenyl)-4H-s-triazolo[4,3-a][1,4]benzodiazepine;

1-[α-(diethylamino)propyl]-6-(m-cyanophenyl)-4H-s-triazolo-[4,3-a][1,4]benzodiazepine;

8-fluoro-1-[(dimethylamino)methyl]-6-phenyl-4H-s-triazolo-[4,3-a][1,4]benzodiazepine;

8-fluoro-1-(aminomethyl)-6-phenyl-4H-s-triazolo-[4,3-a]-[1,4]benzodiazepine;

8-bromo-1[(dimethylamino)methyl]-6-phenyl-4H-s-triazolo-[4,3-a][1,4]benzodiazepine;

8-(trifluoromethyl)-1-[(dimethylamino)methyl]-6-phenyl-4H-s-triazolo[4,3-a][1,4]benzodiazepine;

8-(methylthio)-1-[(dimethylamino)methyl]-6-phenyl-4H-s-triazolo[4,3-a][1,4]benzodiazepine;

1-[(methylamino)methyl]-6-phenyl-4H-s-triazolo[4,3-a][1,4]benzodiazepine;

8-chloro-1-[(dimethylamino)methyl]-6-(o-fluorophenyl)-4H-s-triazolo[4,3-a][1,4]) benzodiazepine;

8-chloro-1-[(diethylamino)methyl]-6-(o-chlorophenyl)-4H-s-triazolo[4,3-a][1,4]benzodiazepine;

8-chloro-1-[(methylamino)methyl]-6-(o-chlorophenyl)-4H-s-triazolo[4,3-a][1,4]benzodiazepine;

8-chloro-1-[α-(dimethylamino)ethyl]-6-phenyl-4H-s-triazolo[4,3-a][1,4]benzodiazepine;

8-chloro-1-[α-(methylamino)ethyl]-6-phenyl-4H-s-triazolo-[4,3-a][1,4]benzodiazepine;
8-chloro-1-[α-aminoethyl)-6-phenyl-4H-s-triazolo[4,3-a]-[1,4]benzodiazepine;
1-[α-(dimethylamino)ethyl]-6-(o-fluorophenyl)-4H-s-triazolo[4,3-a][1,4]benzodiazepine;
1-[α-(dimethylamino)ethyl]-6-(o-chlorophenyl)-4H-s-triazolo[4,3-a][1,4]benzodiazepine;
1-[α-(methylamino)ethyl]-6-(o-chlorophenyl)-4H-s-tri

I claim:

1. 1-(Aminoalkyl)subustituted-6-phenyl-4H-s-triazolo[4,3-a][1,4]-benzodiazepines of the Formula II:

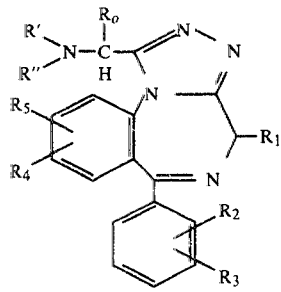

wherein $R_o$ is hydrogen; wherein R′ and R″ are alkyl of one to three carbon atoms, inclusive; wherein $R_1$ is selected from the group consisting of hydrogen and alkyl defined as above; wherein $R_2$, $R_3$, $R_4$, and $R_5$ are selected from the group consisting of hydrogen, alkyl as defined above, halogen, nitro, cyano, trifluoromethyl, and alkoxy, alkylthio, alkylsulfinyl, and alkylsulfonyl, in which the carbon chain moieties are of one to three carbon atoms, inclusive; and the pharmacologically acceptable acid addition salts thereof.

2. A compound according to claim 1, having the Formula III

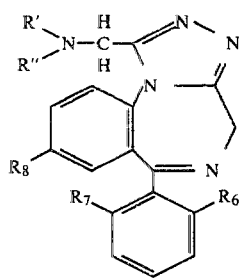

wherein R′ and R″ are alkyl of one to three carbon atoms, inclusive; $R_6$ and $R_7$ are selected from the group consisting of hydrogen, fluorine, chlorine, and bromine; and wherein $R_8$ is selected from the group consisting of hydrogen, fluorine, chlorine, bromine, —CN, —NO$_2$, —CF$_3$, and alkylthio in which the alkyl is defined as above, and the pharmacologically acceptable acid addition salts thereof.

3. A compound according to claim 1 having the formula IV

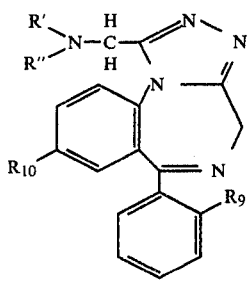

wherein R′ and R″ are alkyl of one to three carbon atoms, inclusive and $R_9$ and $R_{10}$ are selected from the group consisting of hydrogen and chlorine, and the pharmacologically acceptable acid addition salts thereof.

4. A compound according to claim 3 wherein R′ and R″ are methyl, $R_9$ is hydrogen, $R_{10}$ is chloro and the compound is therefore 8-chloro-1-(dimethylamino)-methyl-6-phenyl-4H-s-triazolo[4,3-a][1,4]benzodiazepine.

5. A compound according to claim 3 as a methanesulfonic acid addition salt wherein R′ and R″ are methyl, $R_9$ is hydrogen, $R_{10}$ is chloro and the compound is therefore 8-chloro-1-[(dimethylamino)methyl]-6-phenyl-4H-s-triazolo-[4,3-a][1,4]benzodiazepine methanesulfonate.

6. A compound according to claim 3 wherein R′ and R″ are methyl $R_9$ and $R_{10}$ are chloro and the compound is therefore 8-chloro-1-[(dimethylamino)methyl]-6-(o-chloro-phenyl)-4H-s-triazolo[4,3-a][1,4]benzodiazepine.

7. A compound according to claim 3 wherein R′ and R″ are methyl, $R_{10}$ is hydrogen and $R_9$ is chloro and the compound is therefore 1-(dimethylamino)methyl-6-(o-chlorophenyl)-4H-s-triazolo[4,3-a][1,4]benzodiazepine.

8. A compound according to claim 3 wherein R′ and R″ are ethyl $R_9$ is hydrogen, $R_{10}$ is chloro and the compound is therefore 8-chloro-1-(diethylamino)methyl-6-phenyl-4H-s-triazolo[4,3-a][1,4]benzodiazenine.

9. A compound according to claim 2 wherein R′ and R″ are methyl, $R_7$ is hydrogen, $R_6$ is chloro $R_8$ is nitro and the compound is therefore 8-nitro-1-[(dimethylamino)-methyl)-6-(o-chlorophenyl)-4H-s-triazolo[4,3-a][1,4]benzodiazepine.

10. A compound according to claim 1, wherein R′ and R″ are methyl, $R_1$ and $R_5$ are hydrogen, $R_2$ and $R_3$ are 2- and 6-fluoro $R_4$ is 8-chloro and the compound is therefore 8-chloro-1-[(dimethylamino)methyl]-6-(2,6-difluorophenyl)-4H-s-triazolo[4,3-a][1,4]benzodiazepine.

11. A compound according to claim 3 wherein $R_9$ and $R_{10}$ are hydrogen and R′ and R″ are methyl and the compound is therefore 1-[(dimethylamino)methyl]-6-phenyl-4H-s-triazolo[4,3-a][1,4]benzodiazepine.

* * * * *

UNITED STATES PATENT AND TRADEMARK OFFICE
CERTIFICATE OF CORRECTION

PATENT NO. : 4,250,094  Page 1 of 3
DATED : February 10, 1981
INVENTOR(S) : Jackson B. Hester, Jr.

It is certified that error appears in the above—identified patent and that said Letters Patent is hereby corrected as shown below:

Column 4, line 9; change "oxotermorine" to --oxotremorine--.

Column 4, Table III, line 67; add "50".

line 68; add ">50".

Column 5, line 3; delete "Irpindole" and ">50".

Column 7, line 50; change "(7.5 ml.) to --(75 ml.)--.

Column 11, line 11; change "[4,1]" to --[1,4]--.

Column 13, line 37: change "[1,4-" to --[1,4]- --.

line 41; change "[1,4-" to --[1,4]- --.

line 45; change "heated to a reflux" to --heated to reflux--.

line 47; change "[1,4)" to --[1,4]--.

line 61; change "[1,4-" to --[1,4]--.

line 68; change "...tri-azolo..." to --...triazolo...--.

Column 15, line 18, change "isoproplsulfinyl" to --isopropylsulfinyl--.

line 26; change "[1,4-" to --[1,4]--.

line 68; change "N, 22.90" to --N, 22.80--.

Column 16, line 44; change "[4,3-e]" to --[4,3-a]--.

UNITED STATES PATENT AND TRADEMARK OFFICE
CERTIFICATE OF CORRECTION

PATENT NO. : 4,250,094
DATED : February 10, 1981
INVENTOR(S) : Jackson B. Hester, Jr.

It is certified that error appears in the above—identified patent and that said Letters Patent is hereby corrected as shown below:

Column 17, line 9; all of Specification Page 33 was omitted; add (before the Claims) as follows:

--azolo[4,3-a][1,4]benzodiazepine;

1-[α-(dimethylamino)ethyl]-6-phenyl-4H-s-triazolo[4,3-a][1,4]-benzodiazepine;

1-(α-aminoethyl)-6-phenyl-4H-s-triazolo[4,3-a][1,4]benzodiazepine; and the like.

The novel compounds of formulae II, III, and IV can be reacted with selected acids e.g., hydrochloric, hydrobromic, hydriodic, sulfuric, phosphoric, tartaric, citric, lactic, cyclohexanesulfamic, methanesulfonic, toluenesulfonic and other acids to give the corresponding pharmaceutically acceptable acid addition salts. This reaction is carried out under conventional conditions, in solvents such as ether, dioxane, tetrahydrofuran and the like at room temperatures, and the resulting precipitated salts are collected by filtration.

The novel compounds of formulae II, III, and IV can also be reacted with a peracid, for example, peracetic acid, perbenzoic acid, m-chloroperbenzoic acid, and the like to give the corresponding N-oxides. This reaction is carried out under conventional conditions in solvents such as methanol, ethanol, ether, tetrahydrofuran, dioxane, and the like at room temperature, and the resulting N-oxides are collected by filtration.--

UNITED STATES PATENT AND TRADEMARK OFFICE
CERTIFICATE OF CORRECTION

PATENT NO. : 4,250,094
DATED : February 10, 1981
INVENTOR(S) : Jackson B. Hester, Jr.

It is certified that error appears in the above—identified patent and that said Letters Patent is hereby corrected as shown below:

Column 18, line 43, (Claim 8); change "benzodiazenine" to --benzodiazepine--.

Signed and Sealed this

Nineteenth Day of January 1982

[SEAL]

Attest:

GERALD J. MOSSINGHOFF

Attesting Officer

Commissioner of Patents and Trademarks